US011181534B2

(12) United States Patent
Johnsen et al.

(10) Patent No.: US 11,181,534 B2
(45) Date of Patent: Nov. 23, 2021

(54) ROUTINE LABORATORY AND POINT-OF-CARE (POC) TESTING FOR HEMOSTASIS

(71) Applicant: Bloodworks, Seattle, WA (US)

(72) Inventors: Jill Marie Johnsen, Seattle, WA (US); Barbara A. Konkle, Seattle, WA (US)

(73) Assignee: Bloodworks, Seattle, WA (US)

( * ) Notice: Subject to any disclaimer, the term of this patent is extended or adjusted under 35 U.S.C. 154(b) by 714 days.

(21) Appl. No.: 15/301,943

(22) PCT Filed: Apr. 6, 2015

(86) PCT No.: PCT/US2015/024577
§ 371 (c)(1),
(2) Date: Oct. 4, 2016

(87) PCT Pub. No.: WO2015/154090
PCT Pub. Date: Oct. 8, 2015

(65) Prior Publication Data
US 2017/0184617 A1    Jun. 29, 2017

Related U.S. Application Data

(60) Provisional application No. 61/975,654, filed on Apr. 4, 2014.

(51) Int. Cl.
*G01N 33/86* (2006.01)
*A61K 38/36* (2006.01)
(Continued)

(52) U.S. Cl.
CPC ............. *G01N 33/86* (2013.01); *A61K 38/36* (2013.01); *A61K 38/37* (2013.01); *G01N 33/48* (2013.01);
(Continued)

(58) Field of Classification Search
CPC ........ G01N 33/86; G01N 33/50; G01N 33/48; G01N 2333/745; G01N 2333/755;
(Continued)

(56) References Cited

U.S. PATENT DOCUMENTS 6,242,173 B1 * 6/2001 Mann .................... G01N 33/573
435/13
7,632,921 B2 * 12/2009 Pan ....................... C07K 14/755
530/383
(Continued)

FOREIGN PATENT DOCUMENTS

WO     WO 1999/047907 A1    9/1999
WO     WO 2010/088547 A1    8/2010
(Continued)

OTHER PUBLICATIONS

PCT International Search Report and Written Opinion, International Application No. PCT/US2015/024577, dated Jun. 26, 2015, 19 Pages.
(Continued)

*Primary Examiner* — Allison M Fox
*Assistant Examiner* — Qing Xu
(74) *Attorney, Agent, or Firm* — Lee & Hayes PC; C. Rachal Winger; Thu Nguyen

(57) ABSTRACT

Compositions and methods useful for point of care testing for hemophilia by measuring coagulation factor levels are provided.

22 Claims, 1 Drawing Sheet

(51) Int. Cl.
  A61K 38/37     (2006.01)
  G01N 33/48     (2006.01)
  G01N 33/50     (2006.01)
  G01N 33/577    (2006.01)
  G01N 33/52     (2006.01)
(52) U.S. Cl.
  CPC ............. *G01N 33/50* (2013.01); *G01N 33/52* (2013.01); *G01N 33/577* (2013.01); *G01N 2333/745* (2013.01); *G01N 2333/755* (2013.01); *G01N 2800/224* (2013.01); *G01N 2800/52* (2013.01)
(58) Field of Classification Search
  CPC ....... G01N 2333/435; G01N 2800/224; G01N 2800/52; A61K 38/36; A61K 38/37
  See application file for complete search history.

(56) References Cited

U.S. PATENT DOCUMENTS

| | | | |
|---|---|---|---|
| 8,252,913 B2 | 8/2012 | Schaub et al. | |
| 2009/0215070 A1* | 8/2009 | Parhami-Seren | C07K 16/36 435/7.1 |
| 2010/0129841 A1 | 5/2010 | Lassen et al. | |
| 2011/0046060 A1* | 2/2011 | Schellenberger | C12Y 304/21022 514/13.7 |
| 2012/0231485 A1 | 9/2012 | Onundarson et al. | |
| 2012/0308540 A1* | 12/2012 | Madison | C12N 9/644 424/93.72 |
| 2012/0329082 A1 | 12/2012 | Viola et al. | |
| 2013/0288387 A1 | 10/2013 | Blancher et al. | |
| 2014/0142979 A1 | 5/2014 | Mitsunaga | |
| 2014/0379629 A1 | 12/2014 | Loew-Baselli et al. | |
| 2018/0218782 A1 | 8/2018 | Spotts et al. | |

FOREIGN PATENT DOCUMENTS

| | | |
|---|---|---|
| WO | WO 2014/018777 A2 | 1/2014 |
| WO | WO2015085276 A1 | 6/2015 |

OTHER PUBLICATIONS

"Using myPKFiT(R)," Takeda Pharmaceutical Company Limited, [online], [Accessed Dec. 27, 2020]. 8 pages.
"TRxF Intelligent Dosing System(TM)", Records Processed under FOIA Request # 2015-8339, released by Food and Drug Administration Center for Devices and Radiological Health, 2015, 302 pages.
Adcock, et al., "Advantages, disadvantages and optimization of one-stage and chromogenic factor activity assays in haemophilia A and B," Int. J. Lab. Hematol., vol. 40, No. 6, 2018, pp. 621-629.
Bauman, et al., "Accuracy of the CoaguChek XS for point-of-care international normalized ratio (INR) measurement in children requiring warfarin," Thrombosis and Haemostasis, vol. 99, No. 6, 2008, pp. 1097-1103.
Baxter International Inc., "Exhibit 99.1," 2015, www.sec.gov/Archives/edgar/data/1620546/000119312515126251/d829725dex991.htm#toc. [Accessed Dec. 27, 2020].
Bjorkman & Ahlen, "Population pharmacokinetics of plasma-derived factor IX in adult patients with haemophilia B: implications for dosing in prophylaxis," Pharmacokinetics and Disposition, vol. 68, 2012, pp. 969-977.
Bjorkman, "Evaluation of the TCIWorks Bayesian computer program for estimation of individual pharmacokinetics of FVIII," Haemophilia, vol. 17, 2011, pp. e239-e240.
Bjorkman, "Limited blood sampling for pharmacokinetic dose tailoring of FVIII in the prophylactic treatment of haemophilia A," Haemophilia, vol. 16, No. 4, 2010, pp. 597-605.
Casini, et al., "Dysfibrinogenemia: from molecular anomalies to clinical manifestations and management," J. Thromb. Haemost., vol. 13, No. 6, 2015, pp. 909-919.
Collins, "Personalized prophylaxis," Haemophilia, vol. 18, Suppl. 4, 2012, pp. 131-135.
Collins, et al., "Factor VIII requirement to maintain a target plasma level in the prophylactic treatment of severe hemophilia A: influences of variance in pharmacokinetics and treatment regimens," Journal of Thrombosis and Haemostasis, vol. 8, No. 2, 2010, pp. 269-275.
European Association for Haemophilia and Allied Disorders. Mutation Thr342Met from Factor IX Gene (F9) Variant Database. [online]. Version 1.4. Nov. 2014. [Accessed Feb. 14, 2020]. Available from http://www.factorix.org/.
European Association for Haemophilia and Allied Disorders. Mutation Gln160Arg from Factor VII Gene (F7) Variant Database. [online]. 2010-2020. Version 6.0. May 2019. [Accessed Feb. 14, 2020]. Available from http://www.f7-db.eahad.org/.
Girolami, et al., "Thrombotic and Hemorrhagic Conditions Due to a Gain of Function of Coagulation Proteins: A Special Type of Clotting Disorders," Clin. Appl. Thromb. Hemost., vol. 24, No. 4, 2018, pp. 560-565.
ICON PLC, "The gold standard software in Population Pharmacokinetic and Pharmacokinetic-Pharmacodynamic modelling," iconplc.com/innovation/nonmem/. [Accessed Dec. 27, 2020].
Institute of Structural and Molecular Biology, University College London. Factor XI Deficiency Mutation Database (c). [online]. 2016. [Accessed Feb. 18, 2020]. Available from http://www.factorxi.org/.
ClinicalTrials.gov [Internet]. Bethesda (MD): National Library of Medicine (US). Aug. 19, 2015—. Identifier NCT02528968, National Study of a Pharmacokinetic-Focused Educational Package for Patients With Severe Haemophilia A (UK-PK) ; Jul. 17, 2015; [about 7 screens]. Available from: https://clinicaltrials.gov/ct2/show/record/NCT02528968.
Saito, et al., "Cross-reacting Material-positive Hemophilia A Diagnosed in a Patient with a Spontaneous Thigh Hemorrhage," Intern. Med., vol. 56, No. 13, 2017, pp. 1719-1723.
Saunders, et al., "Factor XI deficiency database: an interactive web database of mutations, phenotypes, and structural analysis tools," Hum. Mutat., vol. 26, No. 3, 2005, pp. 192-198 Abstract Only.
The Medical Advisory Secretariat, "Point-of-Care International Normalized Ratio (INR) Monitoring Devices for Patients on Long-term Oral Anticoagulation Therapy: An Evidence-Based Analysis," Ontario Health Technology Assessment Series, vol. 9, No. 12, 2009, pp. 1-114.
Tripodi, et al., "Position paper on laboratory testing for patients with haemophilia. A consensus document from SISET, AICE, SIBioC and SIPMeL," Blood Transfus., vol. 17, No. 3, 2019, pp. 229-236.
Valentino, "Considerations in individualizing prophylaxis in patients with haemophilia A," Haemophilia, vol. 20, No. 5, 2014, pp. 607-615.

* cited by examiner

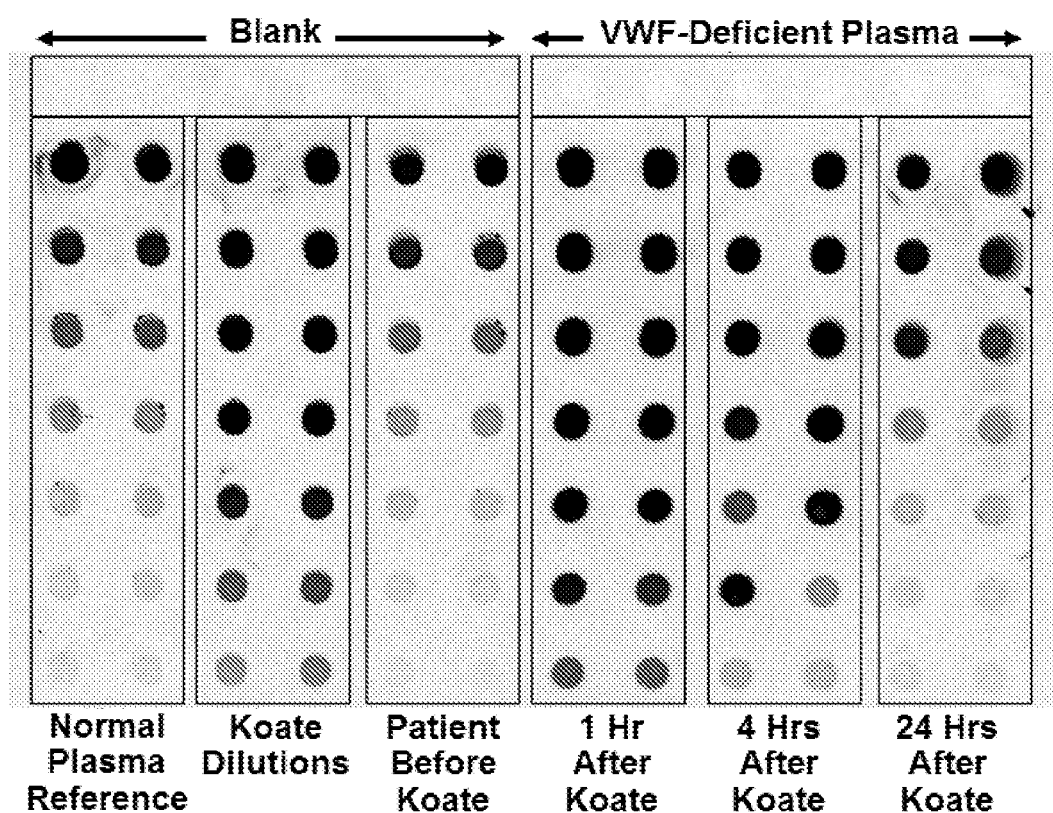

ROUTINE LABORATORY AND POINT-OF-CARE (POC) TESTING FOR HEMOSTASIS

CROSS REFERENCE TO RELATED APPLICATIONS

This application is the National Stage of International Application No. PCT/2015/024577, filed Apr. 6, 2015, and claims the benefit of U.S. Provisional Application No. 61/975,654, filed Apr. 4, 2014, the entire disclosure of which are hereby incorporated by reference in their entirety for all purposes.

BACKGROUND

Field of the Invention

The invention relates compositions and methods useful for clinical laboratory and near-bedside and/or point of care testing for hemostasis (blood clotting) by measuring and determining coagulation factor levels.

Description of the Related Art

Bleeding disorders result from loss of function of one or more clotting factors. Hemophilias are inherited bleeding disorders caused by genetic mutations which affect Factor VIII (FVIII), resulting in Hemophilia A, or Factor IX (FIX), resulting in Hemophilia B. Another common bleeding disorder, von Willebrand Disease (VWD), results from defective or low levels of the coagulation protein von Willebrand Factor (VWF), and can also lead to low FVIII levels. More rarely, mutations in other genes can lead to inherited clinically significant bleeding disorders due to altered function affecting coagulation and fibrinolytic factors, including fibrinogen, fibrin, prothrombin, thrombin, Factor II (FII), Factor V (FV), Factor VII (FVII), Factor X (FX), Factor XI (FXI), Factor XIII (FXIII), Factor XII (FXII), prekallikrein (PK), kallikrein, high molecular weight kininogen (HMWK), Tissue Factor (TF), Tissue Factor Pathway Inhibitor (TFPI), plasminogen, plasmin, plasminogen activator inhibitor-1 and -2 (PAI-1 and PAI-2), antithrombin III (ATIII), protein C (PC), protein S (PS), tissue plasminogen activator (tPA), urokinase, alpha-2 antiplasmin, alpha-2 macroglobulin, thrombin activatable plasmin inhibitor (TAFI), thrombomodulin, and ADAMTS13 (a disintegrin and metalloproteinase with thrombospondin motifs-13). In addition to inherited bleeding disorders, patients can also acquire alterations in coagulation factors which predispose to bleeding as a result of medication exposures (including anti-coagulation drug therapy), medical exposures (including exposure to extracorporeal circuits, artificial valves, vascular shunts, temporary or permanent implantable vascular devices), concurrent medical conditions (including vitamin K deficiency, cancer, liver failure, and renal failure), or the development of antibodies either in response to clotting factor therapy (in which case functional antibodies are termed "inhibitors") or by developing autoantibodies targeting one or more clotting factors (in which case the patient has an "acquired" bleeding disorder).

The current standard of care for treatment for bleeding is to increase the levels of clotting factors circulating in blood to a proscribed level, with the goal of either preventing bleeding (prophylaxis) or to stop ongoing bleeding. Most currently employed drugs are recombinant or plasma-derived clotting factors, although blood products (e.g., plasma, cryoprecipitate) or non-factor drugs (e.g., ddAVP, Amicar/Lysteda) can be used, and drugs targeting coagulation mechanisms (including small molecules and antibody-based strategies) are currently in clinical development. In the special cases where patients have inhibitors or other functional antibodies to clotting factors, therapies include treatment with other "bypassing" clotting factors, non-human (complete or partial) clotting factors (e.g., porcine FVIII), and/or high sustained doses of the target clotting factor in an effort to induce immune tolerance.

Current treatment dosing guidelines are typically calculated based upon the patient's body weight and factor activity levels. Patients can have varied individual responses to replacement therapies, likely in large part due to differences in drug or factor survival, and, in the case of active bleeding, factor consumption. The decision for adjustments in dosing regimens is often empiric and initiated after adverse outcomes (usually bleeding, but also rarely clotting), in which case, the patients must have samples sent to a specialty clinical laboratory to re-test factor activity levels, assess for the development of inhibitors, and/or, rarely, perform kinetic studies. Fundamentally, drug dosing is often based upon previously obtained or historical factor activity levels, which (particularly with newer drugs coming to market or in the setting of active bleeding) may not accurately reflect the real time coagulation factor level of the patient.

Patient dosing regimens are regularly based on previous clotting test activity levels and bleeding history. For patients with mild or moderate bleeding disorders, outpatient treatments are often "on-demand", meaning treatment is provided when bleeding occurs, or when a hemostatically risky event, such as surgery, is anticipated. Patients with more severe bleeding, severely low factor activity levels at baseline, or who choose more physically active lives are often treated more frequently or with scheduled prophylaxis using self-infusions to maintain clotting factors at a level which should prevent many, but not all, sporadic bleeding events.

Unmet Clinical and Scientific Need

We anticipate that with recent advances in drug development and clinical practice, the capability to perform testing outside specialized clinical reference laboratories, particularly near-bedside or point-of-care (POC) testing, for patients with bleeding risks due to inherited or acquired bleeding disorders would greatly enhance safety and efficacy and individualize patient care. New drugs for bleeding disorders show great promise, some of which are designed to be longer acting. New therapeutic agents to the bleeding disorder treatment armamentarium, along with evolving clinical management practices seeking to enable patients to lead more normal active lives, define new needs for bleeding disorder patients. Medically-significant bleeding events are the consequences of under-treatment of bleeding disorders and are expensive and can be disabling or life-threatening. The risks of overtreatment are the unnecessary use of drugs and risk of pathologic clotting. A major obstacle to individualized bleeding disorder care is the inability to use information about coagulation factor levels in real time to inform treatment dose adjustments to achieve goal factor levels reliably, particularly during active bleeding both outpatient and in hospitals and other care facilities without ready access to specialty hemostasis reference laboratories, and to tailor therapies to be responsive to the varied bleeding risks of different activities of daily living. The ability to use factor level information to guide therapy at POC would greatly facilitate care for bleeding disorder patients, and should lead to improved patient outcomes, including less morbidity from joint and muscle bleeding.

The present disclosure provides solutions to these and other needs.

SUMMARY

In one aspect, disclosed herein is a method for determining the level of coagulation factor activity score to determine clotting status in a subject comprising: a) generating data on the level of a coagulation factor in a sample from the subject; b) obtaining data representing the subject's baseline level of the coagulation factor; c) obtaining data representing the subject's baseline level of the coagulation factor activity; d) obtaining data representing the level of a drug coagulation factor; e) obtaining data representing the level of drug coagulation factor activity units; f) obtaining data representing the ratio or coefficient of drug activity units; g) in the event of more than one drug, obtaining the information in d), e), and f) for each additional drug, and h) generating a score by mathematically combining the data in (a)-(g), wherein the score is indicative of clotting status of the subject.

In some embodiments, the score is used per standard clinical practice determine the dose of a drug to be administered to the subject.

In some embodiments, the score is generated by a computer processor.

In some embodiments, the score is the $POC_{Activity}$ of the coagulation determined using the formula: $POC_{Activity} = (Base_{Activity}) + [(Measured_{Ag} - Base_{Ag}) \times (Drug_{Activity:Ag\ Ratio})]$.

In some embodiments, the coagulation factor is Factor VIII (FVIII), Factor IX (FIX), von Willebrand Factor (VWF), fibrinogen, fibrin, prothrombin, thrombin, Factor II (FII), Factor V (FV), Factor VII (FVII), Factor X (FX), Factor XI (FXI), Factor XIII (FXIII), Factor XII (FXII), prekallikrein (PK), kallikrein, high molecular weight kininogen (HMWK), Tissue Factor (TF), Tissue Factor Pathway Inhibitor (TFPI), plasminogen, plasmin, plasminogen activator inhibitor-1 and -2 (PAI-1 and PAI-2), antithrombin III (ATIII), protein C (PC), protein S (PS), tissue plasminogen activator (tPA), urokinase, alpha-2 antiplasmin, alpha-2 macroglobulin, thrombin activatable plasmin inhibitor (TAFI), thrombomodulin, and/or ADAMTS13 (a disintegrin and metalloproteinase with thrombospondin motifs-13).

In some embodiments, the sample is a blood sample or blood component (plasma, serum, blood cells, microparticles), saliva, or urine.

In some embodiments, the level of the coagulation factor is determined using a coagulation-factor specific molecule, which can be a polyclonal antibody or a monoclonal antibody.

In some embodiments, the coagulation-factor specific molecule is a specific substrate for the coagulation factor.

In some embodiments, the coagulation-factor specific molecule is a specific ligand for the coagulation factor.

In some embodiments, the coagulation-factor specific molecule is a decoy molecular mimic of the coagulation factor substrate or ligand.

In some embodiments, the coagulation-factor specific molecule is a small molecule compound.

In some embodiments, the coagulation-factor specific molecule is a lectin.

In some embodiments, the coagulation-factor specific molecule is a nucleotide.

In some embodiments of the above, the coagulation factor is determined using direct detection of the coagulation factor-specific molecule via a linked tag, such as metal, chemical, or fluorescent tag.

In some embodiments of the above, the coagulation factor is determined using secondary detection with an antibody (similar to ELISA, Western blot, or dot blot).

In some embodiments of the above, more than one coagulation factor may be detected at the same time in a multiplex assay.

In some embodiments of the above, more than one coagulation factor may be detected at the same time using multiple parallel assays.

In some embodiments of the above, the drug is a blood component, plasma-derived clotting factor(s), recombinant clotting factor(s), small molecule, and/or antibody.

Also provided herein is a system for determining the level of a coagulation factor activity score from a sample obtained from a subject, the system comprising: a storage memory for storing data, wherein the data comprises a) data on the level of a coagulation factor in a sample from the subject; b) data representing the subject's baseline level of the coagulation factor; c) data representing the subject's baseline level of the coagulation factor activity; d) data representing the level of a drug coagulation factor; e) data representing the level of drug coagulation factor activity units; and f) data representing the ratio or coefficient of drug activity units; and a processor communicatively coupled to the storage memory for generating a score by mathematically combining the data in (a)-(f), wherein the score is indicative of clotting status of the subject.

Also provided herein is a computer-readable storage medium storing computer-executable program code for determining the level of a coagulation factor activity score from a sample obtained from a subject, the medium comprising: data comprising a) data on the level of a coagulation factor in a sample from the subject; b) data representing the subject's baseline level of the coagulation factor; c) data representing the subject's baseline level of the coagulation factor activity; d) data representing the level of a drug coagulation factor; e) data representing the level of drug coagulation factor activity units; and f) data representing the ratio or coefficient of drug activity units; and computer-executable program code for generating a score by mathematically combining the data in (a)-(f), wherein the score is indicative of clotting status of the subject.

BRIEF DESCRIPTION OF THE SEVERAL VIEWS OF THE DRAWINGS

These and other features, aspects, and advantages of the present invention will become better understood with regard to the following description, and accompanying drawing, where:

FIG. 1 shows paper-based detection of VWF antigen.

DETAILED DESCRIPTION

Definitions

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

The term "mammal" encompasses both humans and non-humans and includes, but is not limited to humans, non-human primates, canines, felines, murines, bovines, equines, and porcines.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female.

The term "generating data" encompasses obtaining a set of data determined from at least one sample. Generating data encompasses obtaining a sample, and processing the sample to experimentally determine the data. The phrase also encompasses receiving a set of data, e.g., from a third party that has processed the sample to experimentally determine the data. Additionally, the phrase encompasses mining data from at least one database or at least one publication or a combination of databases and publications. Data can be obtained by one of skill in the art via a variety of known ways including stored on a storage memory. Obtaining data encompasses data which has been generated from a sample, or data which has been obtained from sources such as patient medical history and records, physical examinations, treatment history, and the like.

The term "clinical factor" refers to a measure of a condition of a subject, e.g., disease activity or severity. "Clinical factor" encompasses all indicators of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition.

The term "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, coagulation factor value transformations and normalizations (including, without limitation, normalization schemes that are based on clinical parameters such as age, gender, ethnicity, etc.), rules and guidelines, statistical classification models, and neural networks trained on populations. Also of use in the context of coagulation factors are linear and non-linear equations and statistical classification analyses to determine the relationship between (a) levels of coagulation factors detected in a subject sample and (b) the level of the respective subject's disease activity.

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements.

To "analyze" includes determining a value or set of values associated with a sample by measurement of analyte levels in the sample. "Analyze" may further comprise and comparing the levels against constituent levels in a sample or set of samples from the same subject or other subject(s). For example, the coagulation factors of the present teachings can be analyzed by any of various conventional methods known in the art.

The term "antibody" refers to any immunoglobulin-like molecule that binds to an epitope with the required selectivity. Thus, the term includes any such molecule that is capable of selectively binding to a coagulation factor of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific and multi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, $F_v$ fragments, single chain $F_v$ fragments, nanobodies, and chimeras comprising an immunoglobulin sequence and any modifications of the foregoing that comprise an antigen recognition site of the required selectivity.

The term "coagulation factor" refers generally to a factor which participates in achieving hemostasis and/or clot formation in vivo. Examples of coagulation factors include, but are not limited to Factor VIII (FVIII), Factor IX (FIX), fibrinogen, fibrin, prothrombin, thrombin, Factor II (FII), Factor V (FV), Factor VII (FVII), Factor X (FX), Factor XI (FXI), Factor XIII (FXIII), von Willebrand Factor (VWF), Factor XII (FXII), prekallikrein (PK), kallikrein, high molecular weight kininogen (HMWK), Tissue Factor (TF), Tissue Factor Pathway Inhibitor (TFPI), plasminogen, plasmin, plasminogen activator inhibitor-1 and -2 (PAI-1 and PAI-2), antithrombin III (ATIII), protein C (PC), protein S (PS), tissue plasminogen activator (tPA), urokinase, alpha-2 antiplasmin, alpha-2 macroglobulin, thrombin activatable plasmin inhibitor (TAFI), thrombomodulin, ADAMTS13 (a disintegrin and metalloproteinase with thrombospondin motifs-13). Derivatives of coagulation factors can include forms which are activated, cleaved, or inhibited/inactivated.

"Coagulation factor level" or "Coagulation factor measured at POC (Measured$_{Ag}$)" refers generally to the level (quantity) of a coagulation factor in a sample. As used herein, this is generally a measure of the level of the protein via specific molecular interactions, however, the measure of other analytes related to a coagulation factor level, such as its mRNA can be used. This measurement can be done in routine laboratories and at point of care (POC).

"Calculated factor activity at POC (POC$_{Activity}$)" refers generally to the level of the coagulation factor determined by the methods disclosed herein, in which a measured coagulation factor level is used in conjunction with additional data previously measured, calculated, or known and includes the patient's baseline factor activity, baseline factor level, drugs the patient has received, and information about each drug (drug coefficient, timing, and drug kinetics, if known).

"Baseline level of coagulation factor" or "Patient's baseline (historical/diagnosis) coagulation factor (Base$_{Ag}$)" refers generally to the coagulation factor level measured in the absence of treatment or bleeding.

"Calculated baseline level of coagulation factor" or "Patient's calculated coagulation factor (Base$_{Ag}$)" refers to the calculation of the baseline coagulation factor based upon clinical/historical and measured data similar as disclosed herein.

"Baseline level of coagulation factor activity" or "Patient's baseline (historical/diagnosis) coagulation factor activity units (Base$_{Activity}$)" refers generally to the coagulation factor activity measured in the absence of treatment or bleeding.

"Level of drug coagulation factor" or "Drug coagulation factor (Drug$_{Ag}$)" refers generally to the measurable coagulation factor of a drug in plasma or recovered in vivo.

Examples of drug coagulation factors include, but are not limited to the factor replacement products listed below.

| Coagulation Factor Replaced | Product by Brand Name | Marketing Company |
|---|---|---|
| Factor VIII | Advate | Baxter |
| | Recombinate | Baxter |
| | Hemofil M | Baxter |
| | Kogenate FS | Bayer |
| | Eloctate | Biogen-Idec |
| | Helixate FS | CSL Behring |
| | Monoclate P | CSL Behring |
| | Xyntha | Pfizer |
| Porcine FVIII | Obizur | Baxter |
| Factor VIII and VWF | Humate P | CSL Behring |
| | Alphanate | Grifols |
| | Koate DVI-DVI* | Kedrion |
| | Wilate** | Octapharma |
| Factor IX | Rixubis | Baxter |
| | Alprolix | Biogen-Idec |
| | Mononine | CSL Behring |
| | BeneFIX | Pfizer |
| Fibrinogen | RiaSTAP | CSL Behring |
| FVIIa | NovoSeven RT | Novo Nordisk |
| FXIII | Corifact | CSL Behring |
| | Tretten | Novo Nordisk |
| Antithrombin | Thrombate | Grifols |
| | ATryn | GTC Biotherapeutics |

*Not FDA approved for VWF replacement in VWD
**Not FDA approved for FVIII replacement in Hemophilia A "Level of drug coagulation factor activity" or "Drug coagulation factor activity units ($Drug_{Activity}$)" refers generally to measurement of an enzyme activity and/or ligand interaction key to the function of the coagulation factor.

"Ratio or coefficient of drug activity units" or "Known ratio of drug activity units:drug level ($Drug_{Activity:Ag\ Ratio}$)" refers generally to a linear or non-linear coefficient derived from the measured drug or therapeutic factor activity relative to measured drug or therapeutic factor.

The term "coagulation factor activity score" refers generally to the calculated factor activity derived from the measured factor level, drug coefficient(s), patient's baseline factor activity, and patient's baseline factor level.

The term "clotting factor status" refers generally to the presence of hemostatically active factor, generally measured currently by coagulation factor activity or ligand assays.

The term "decoy molecular mimic" refers to a molecule which presents epitopes and/or molecular structures which interact with the coagulation factor in the same or similar manner as the natural ligand or substrate, but are not the natural ligand or substrate.

It must be noted that, as used in the specification and the appended claims, the singular forms "a," "an," and "the" include plural referents unless the context clearly dictates otherwise.

Current Methods and Shortcomings

Current testing methods for bleeding disorders are, with few exceptions, based upon assays that determine the activity of clotting factors. Coagulation factor levels are rarely used for the diagnosis of bleeding disorders as some patients carry disease-causing mutations or acquire changes in clotting factors that results in loss-of-function of a specific clotting factor activity relative to the factor level. Thus, coagulation factor activity assays are the mainstay of diagnostic evaluations for most bleeding disorders, and these activity assays have also been adopted for the purposes of disease monitoring and response to treatment.

Clotting factor activity assays are performed in highly specialized clinical laboratories owing to the fact that assays of clotting factor activities are time consuming and technically challenging due to artifactual activation of the clotting cascade ex vivo. Previous attempts to develop routine clinical laboratory (non-reference laboratory) and POC clotting factor activity capabilities have been unsuccessful, except for POC INR monitoring for warfarin therapy. Although clotting factor antigen assays exist (largely as enzyme-linked immunosorbent assays, or ELISAs), they are rarely used in clinical decision making in favor of direct activity measures. However, we have discovered that clotting factor activity values while sufficient, are not necessary for the purposes of treatment decisions in a well-characterized bleeding disorder patient. We instead have discovered that clotting factor level measurement can be used in an accessible and POC-amenable manner for individualized bleeding patient care.

Disclosed herein is a new method to utilize POC-amenable coagulation factor level data in patients with diagnosed bleeding disorders for disease monitoring and therapeutic decision making.

The method will use measured coagulation factor values to calculate the patient's real time coagulation factor activity using data known about the patient's baseline (diagnosis) factor deficiency and drug exposures. The following sample calculation illustrates the basis of the envisioned application of the proposed method to determine routine drug dosing for factors with a normalized (plasma-only) volume of distribution (which is true for nearly all coagulation factors):

Terms
Coagulation factor measured at POC=$Measured_{Ag}$
Calculated factor activity at POC=$POC_{Activity}$
Patient's baseline (historical/diagnosis) coagulation factor $Base_{Ag}$
Patient's baseline (historical/diagnosis) coagulation factor activity units=$BaSe_{Activity}$
Drug coagulation factor level=$Drug_{Ag}$
Drug coagulation factor activity units=$Drug_{Activity}$
Known ratio of drug activity units:drug levl=$Drug_{Activity:Ag\ Ratio}$ The measured coagulation factor level in circulation in the stable patient is:

$$Measured_{Ag}=Base_{Ag}+Drug_{Ag}$$

The amount of drug factor protein present in circulation would then be:

$$Drug_{Ag}=Measured_{Ag}-Base_{Ag}$$

The amount of drug coagulation factor activity in circulation can then be calculated by:

$$Drug_{Activity}=Drug_{Ag}\times(Drug_{Activity:Ag\ Ratio})$$

The measured coagulation factor level in circulation in the hemostatically stable and medically simple coagulation-deficiency patient is:

$$POC_{Activity}=(Base_{Activity})+(Drug_{Activity})$$

$POC_{Activity}$ will be used to monitor disease/inhibitors and to facilitate individualized and flexible therapy. Algorithms personalized for each patient would use the $POC_{Activity}$ and the patient's weight to calculate the dose of specific drugs to be infused. Dosing will target drug factor levels to be determined based upon standard clinical practice for the patient's specific bleeding disorder diagnosis and ranked imminent hemostatic risk (active severe bleeding, active minor bleeding, activity or procedure with high risk for bleeding, low risk for bleeding, etc.). Algorithms can be further adjusted using additional serial $POC_{Activity}$ determinations and clinical response to monitor and adjust therapy.

As understood by those of skill in the art, the example method above may require additional linear or higher-order coefficients to correct for empiric observations at steady-state. This method may need to be further adapted in the actively bleeding patient, who is consuming coagulation factors, using corrections determined by empiric measurement of the kinetics of coagulation factor activity vs. antigen for endogenous and drug-delivered coagulation factors. Similarly, variations on the method could be used in the setting of multiple drug exposures (e.g. a patient with both a short and long-acting drug on board) by using the patient's dosing history, the $Drug_{Activity:Ag\ Ratio}$ for all drugs, and the drug half-lives to calculate residual drug levels (and therefore the $POC_{Activity}$) from the $Measured_{Ag}$.

Coagulation factor level determination using this method should be superior to current care as this method can provide data in real time to inform medical decision making. This method permits not only adjustment for confounders such as recent drug therapy and inherent individual variances in drug kinetics, but also would allow timely responsive therapy for active bleeding while being sensitive to underlying disease mechanics. Measures of clotting factor levels for the purposes of therapeutic decision making is a capability currently only available to inpatients with close proximity to highly specialized clinical laboratories able to perform the coagulation factor activity assays, which can take hours to obtain results.

This capability will provide patients the ability to use factor much more effectively during normal activities (which requires lower levels for most patients) while enabling the patient to more safely self-administer appropriate dosing customized for higher risk activities, such as sports, dental procedures, admissions to rural hospitals, etc. Furthermore, treatment of outpatient bleeding is likely to become more effective in controlling bleeding and transitions to healing. Additionally, given the speed at which a POC clotting factor level is anticipated to be obtained with current and emergent technologies, this method would likely be highly useful in the inpatient setting, and perhaps preferable to frequent STAT coagulation factor testing in the reference laboratory.

Measurement of Coagulation Factors

The quantity of one or more coagulation factors of the present teachings can be indicated as a value. The value can be one or more numerical values resulting from the evaluation of a sample, and can be derived, e.g., by measuring level(s) of the coagulation factor(s) in a sample by an assay performed in a laboratory, or from data obtained from a provider such as a laboratory, or from data stored on a server. Coagulation factor levels can be measured using any of several techniques known in the art, such as those described herein.

The measurement of levels of the coagulation factor can be determined at the protein, glycan, lipid, small molecule/ metabolome, or nucleic acid level using any method known in the art. "Protein" detection comprises detection of full-length proteins, mature proteins, pre-proteins, polypeptides, isoforms, mutations, variants, post-translationally modified proteins and variants thereof, and can be detected in any suitable manner. Levels of coagulation factor can be determined at the protein level, e.g., by measuring the serum levels of peptides encoded by the gene products described herein, or by measuring the enzymatic activities of these protein coagulation factors. Such methods are well-known in the art and include, e.g., immunoassays based on antibodies to proteins encoded by the genes, aptamers or molecular imprints. Any biological material can be used for the detection/quantification of the protein. Alternatively, a suitable method can be selected to determine the activity of proteins encoded by the coagulation factor genes according to the activity of each protein analyzed. For coagulation factor proteins, polypeptides, isoforms, mutations, and variants thereof known to have enzymatic activity, the activities can be determined in vitro using enzyme assays known in the art, particularly for this method via detection of the molecular interaction of the coagulation factor with its ligand(s), ligand derivative(s) (including polypeptide(s), cleavage product(s)), molecular decoy(s), small molecule(s), carbohydrate(s), lectin(s), lipid(s), glycolipid(s), phospholipids(s), nucleotides(s).

Using sequence information provided by the public database entries for the coagulation factor, expression of the coagulation factor can be detected and measured using techniques well-known to those of skill in the art. For example, nucleic acid sequences in the sequence databases that correspond to nucleic acids of coagulation factors can be used to construct primers and probes for detecting and/or measuring coagulation factor nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying coagulation factor sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed coagulation factor mRNA sequences reverse-transcribe the mRNA into DNA, which is then amplified in PCR and can be visualized and quantified. Coagulation factor RNA can also be quantified using, for example, other target amplification methods, such as TMA, SDA, and NASBA, or signal amplification methods (e.g., bDNA), and the like. Ribonuclease protection assays can also be used, using probes that specifically recognize one or more coagulation factor mRNA sequences, to determine gene expression.

Alternatively, coagulation factor protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other coagulation factor analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other coagulation factor metabolites can be similarly detected using reagents that are specifically designed or tailored to detect such metabolites.

In some embodiments, a coagulation factor is detected by contacting a subject sample with reagents, generating complexes of reagent and analyte, and detecting the complexes. Examples of "reagents" include but are not limited to nucleic acid primers, peptides, small molecules, and antibodies.

In some embodiments of the present teachings an antibody binding assay is used to detect a coagulation factor; e.g., a sample from the subject is contacted with an antibody reagent that binds the coagulation factor analyte, a reaction product (or complex) comprising the antibody reagent and analyte is generated, and the presence (or absence) or amount of the complex is determined. The antibody reagent useful in detecting coagulation factor analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. In a homogeneous assay the immunological reaction can involve the specific antibody (e.g., anti-coagulation factor protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the coagulation factor in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the coagulation factor in the test sample. Examples of suitable immunoassays include but are not limited to oligonucleotides, immunoblotting, immunoprecipitation, immunofluorescence methods, chemiluminescence methods, electrochemiluminescence (ECL), and/or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, Fla. See also U.S. Pat. No. 4,727,022 to C. Skold et al., titled "Novel Methods for Modulating Ligand-Receptor Interactions and their Application"; U.S. Pat. No. 4,659,678 to G C Forrest et al., titled "Immunoassay of Antigens"; U.S. Pat. No. 4,376,110 to G S David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230,797 to R. Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of coagulation factors. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10): 1445-1451.

The information from the assays above can be quantitative and sent to a computer system of the invention. The information can also be qualitative, such as observing patterns or fluorescence, which can be translated into a quantitative measure by a user or automatically by a reader or computer system. In an embodiment, the subject can also provide information other than assay information to a computer system, such as race, height, weight, age, gender, eye color, hair color, family medical history and any other information that may be useful to a user, such as a clinical factor described above.

Kits

Other embodiments of the present teachings comprise coagulation factor detection reagents packaged together in the form of a kit for conducting any of the assays of the present teachings. In certain embodiments, the kits comprise reagents for protein detection of coagulation factor proteins, such as antibodies. For example, the kit may comprise antibodies or fragments thereof, specific for coagulation factors (primary antibodies), along with one or more secondary antibodies that may incorporate a detectable label; such antibodies may be used in an assay such as an ELISA. Alternately, the antibodies or fragments thereof may be fixed to a solid surface, e.g. an antibody array. In certain embodiments, the kits comprise oligonucleotides that specifically identify one or more coagulation factor nucleic acids based on homology and/or complementarity with coagulation factor nucleic acids. The oligonucleotide sequences may correspond to fragments of the coagulation factor nucleic acids. For example, the oligonucleotides can be more than 200, 200, 150, 100, 50, 25, 10, or fewer than 10 nucleotides in length. In other embodiments, the kits comprise antibodies to proteins encoded by the coagulation factor nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a DAI score, can be included in the kit; e.g., written, tape, VCR, or CD-ROM. The assay can for example be in the form of a Northern hybridization or a sandwich ELISA as known in the art.

In some embodiments of the present teachings, coagulation factor detection reagents can be immobilized on a solid matrix, such as a porous strip, to form at least one coagulation factor detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of coagulation factor present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B(1992).

Example 1: Determination of Factor VIII (FVIII)

Patients with Hemophilia A are deficient in the coagulation protein Factor VIII (FVIII). We determined the FVIII Activity levels in patients with Hemophilia A using FVIII Activity and FVIII Antigen data in conjunction with data regarding bleeding disorder drugs.

Measurement of FVIII

Blood samples were collected by venipuncture in 3.2% sodium citrate anticoagulant. Platelet poor plasma was separated by centrifugation per clinical protocols, snap frozen, and stored at −80 C until tested. FVIII Antigen was measured by ELISA (FVIII-AG ELISA kit, Affinity Biologicals) per the manufacturer's instructions. FVIII Activity was measured by manual one-stage assay per the clinical protocol of the Bloodworks Northwest Hemostasis Reference Laboratory. The Koate DVI (Kedrion) coefficient (in vivo) was ascertained by measuring FVIII Antigen and FVIII Activity samples from patients undergoing clinically-indicated Koate DVI kinetic studies and calculating the Activity: Antigen ratio. Pooled normal plasma (Precision BioLogic), normal reference plasmas (Precision BioLogic, Siemens), abnormal reference plasma (Siemens), samples from healthy blood donors, and FVIII-deficient plasma (Affinity Biologicals, Siemens) were used in assays as standards and controls.

Determination of FVIII Levels in Patients with Hemophilia A

FVIII Case #1

A 24 year old male with severe hemophilia A presented for a clinically-indicated kinetic study of Koate DVI. His historical FVIII Activity was <1% at baseline. The patient had blood samples drawn at baseline (without drug) and then one hour and 24 hours after infusion of Koate DVI, a FVIII replacement drug. The patient's baseline FVIII Activity was <1%, and his baseline FVIII Antigen was 1.01 IU/dL. One hour after Koate DVI, his FVIII Antigen was measured to be 83.65 IU/dL, and 24 hours after Koate DVI his FVIII Antigen was measured to be 0.32 IU/dL. We experimentally determined the Koate DVI drug coefficient to be 1.08. The baseline Factor VIII Activity was set to 0%.

We then used this information to determine the patient's FVIII Activity as follows: FVIII Activity=(Base FVIII Activity)+[(Measured FVIII Antigen−Base FVIII Antigen)×(Koate DVI Drug Coefficient)]. Thus, at each time point after Koate DVI, we determined his FVIII Activity to be:

1 hour time point: 0%+[(83.65 IU/dL−1.01 IU/dL)×(1.08)]=89.25% FVIII Activity 24 hour time point: 0%+[(0.32 IU/dL−1.01 IU/dL)×(1.08)]=−0.745% FVIII Activity These results were clinically comparable to the measured FVIII activities (Table 1).

FVIII Case #2

A 28 year old male with severe Hemophilia A presented for a clinically indicated kinetic study of Koate DVI, a FVIII replacement therapy. The patient's historical FVIII Activity was <1%. The patient had received a different FVIII replacement drug, Hemofil (Baxter), 22 hours prior to presentation, and no baseline sample was available. The patient's initial blood sample testing measured a FVIII Activity of 2% and a FVIII Antigen of 3.24 IU/dL. The patient received a dose of Koate DVI, and then had blood samples drawn one hour and 24 hours after infusion. At one hour, the FVIII Antigen was measured to be 161.14 IU/dL, and at 24 hours the FVIII Antigen was measured to be 5.04 IU/dL.

We calculated the patient's baseline FVIII Antigen assuming the same drug coefficient for Hemofil as Koate DVI (1.08) due to similar in vitro data regarding the Activity: Antigen ratio. Thus, FVIII Antigen was deduced by: Baseline FVIII Antigen=Measured FVIII Antigen−[(Measured FVIII Activity−Baseline FVIII Activity)/(Drug Coefficient)]. Thusly, the patient's Baseline FVIII Antigen was determined to be: 3.24 IU/dL−[(2%−0%)/1.08]=1.08 IU/dL. The patient's baseline Factor VIII Activity was set to 0%.

We then applied the patient's calculated Baseline FVIII Antigen to determine the patient's FVIII by: FVIII Activity=(Base FVIII Activity)+[(Measured FVIII Antigen−Base FVIII Antigen)×(Koate DVI Drug Coefficient)], and at each time point we determined his FVIII level to be:

For this patient, we determined FVIII to be:

0%+[(161.14 IU/dL−1.08 IU/dL)×(1.08)]=172.86% FVIII Activity

0%+[(5.04 IU/dL−1.08 IU/dL)×(1.08)]=4.28% FVIII Activity

These results were clinically comparable to the measured FVIII activities as shown in Table 2:

TABLE 1

Determination of FVIII in a Patient with Severe Hemophilia A

| Time Point | Baseline FVIII Activity (FVIII:C) | Baseline FVIII Antigen (FVIII:Ag) | Measured FVIII Antigen (FVIII:Ag) (after Koate DVI) | FVIII Activity (Calculated) | FVIII Activity (Measured) |
|---|---|---|---|---|---|
| Baseline | <1% | 1.01 IU/dL | | | |
| 1 hr after Koate DVI | | | 83.65 IU/dL | 89.3% | 88.4% |
| 24 hrs after Koate DVI | | | 0.32 IU/dL | −0.7% | <1% |

TABLE 2

Determination of FVIII in a Different Patient with Severe Hemophilia A

| Time Point | Baseline FVIII Activity (FVIII:C) (Historical) | Baseline FVIII Antigen (FVIII:Ag) (Calculated) | Measured FVIII Antigen (FVIII:Ag) (after Koate DVI) | FVIII Activity (Calculated) | FVIII Activity (Measured) |
|---|---|---|---|---|---|
| Imputed Baseline | <1% | 1.08 IU/dL | | | |
| Before Koate DVI* | | | 3.24 IU/dL | | 2% |
| 1 hr after Koate DVI | | | 161.14 IU/dL | 172.9% | 187% |
| 24 hrs after Koate DVI | | | 5.04 | 4.3% | 4% |

*22 hrs after Hemofil

FVIII Case #3

A 61 year old male with mild Hemophilia A (historical baseline FVIII Activity 14%) presented for a trial of Stimate (CSL Behring), a drug which stimulates release of the body's own stores of FVIII into circulation. Blood samples were drawn at baseline and 45 minutes after Stimate exposure. The patient's baseline FVIII Activity was measured to be 18.9%, and his baseline FVIII Antigen was measured to be 9.59 IU/dL. Forty-five minutes after Stimate, the patient's FVIII Antigen was measured to be 24.83 IU/dL.

The patient's FVIII Coefficient was determined by: Patient FVIII Coefficient=(Baseline FVIII Activity)/(Baseline FVIII Antigen). Therefore, the patient's FVIII Coefficient=(18.9)/(9.59)=1.97. We then determined the patient's FVIII Activity by applying FVIII Activity=(Base FVIII Activity)+[(Measured FVIII Antigen−Base FVIII Antigen)×(Patient's FVIII Coefficient)].

Thus, for this patient we determined the FVIII Activity after Stimate to be: 18.9%+[(24.83 IU/dL−9.59 IU/dL)×(1.97)]=48.92% FVIII Activity These results were clinically comparable to the measured FVIII Activity (Table 3).

TABLE 3

Determination of FVIII in a Patient with Mild Hemophilia A

| Time Point | Baseline FVIII Activity (FVIII:C) | Baseline FVIII Antigen (FVIII:Ag) | Measured FVIII Antigen (FVIII:Ag) (after Stimate) | FVIII Activity (Calculated) | FVIII Activity (Measured) |
|---|---|---|---|---|---|
| Baseline | 18.9% | 9.59 IU/dL | | | |
| 45 min after Stimate | | | 24.83 IU/dL | 48.92% | 50.76% |

Example 2: Determination of Factor IX (FIX)

Deficiencies of the coagulation protein, Factor IX (FIX), result in Hemophilia B. We tested our ability to determine FIX levels in a patient with Hemophilia B using this method.

Measurement of FIX:

Blood samples were collected by venipuncture in 3.2% sodium citrate anticoagulant. Platelet poor plasma was separated by centrifugation per clinical protocols, snap frozen, and stored at −80 C until tested. FIX Antigen was measured by FIX-EIA paired antibody ELISA (Affinity Biologicals). FIX-deficient plasma (Affinity Biologicals) was used as a negative control and diluent. FIX Activity was performed via manual one-stage assay per the clinical laboratory protocols of the Bloodworks Northwest Hemostasis Reference Laboratory. FIX-deficient plasma (Siemens) was used as a diluent and negative control. The Benefix (Wyeth Pharmaceuticals) coefficient was ascertained by serial dilution of Benefix into FIX-deficient plasma (Affinity Biologicals), performance of both the FIX Antigen and Activity assays, and calculating the Activity:Antigen ratio.

Determination of FIX Levels a Patient with Hemophilia B:

FIX Case #1

A 20 year old male with severe Hemophilia B presented for a clinically indicated kinetic study of Alprolix, a FIX replacement therapy. The patient's baseline FIX Activity was reported to be <1%. The patient had received a dose of Benefix, a different FIX replacement therapy, 6 days prior to the clinic visit. At presentation, we measured the FIX Antigen to be 8.0 IU/dL and the FIX Activity to be 4%. The detectable FIX Activity was clinically attributed to persistence of the Benefix in the patient.

We determined the patient's baseline FIX Antigen by using the patient's historical FIX Activity and experimentally determined the drug coefficient of Benefix to be 2.1. We then calculated: Baseline FIX Antigen=Measured FIX Antigen−[(Measured FIX Activity−Baseline FIX Activity)/(Benefix Drug Coefficient)]. Therefore, the patient's Baseline FIX Antigen was calculated to be: 8.0 IU/dL−[(4%−0%)/2.1]=6.1 IU/dL.

The patient then received a dose of Alprolix followed by a blood draw 24 hours later. The Alprolix drug coefficient was not able to be experimentally determined due to limited drug availability. In lieu of this, we used normal plasma standards and experimentally determined the coefficient of normal human FIX to be 1.1. We then assumed the drug coefficient for Alprolix to be similar to naturally occurring FIX, and determined the patient's FIX level by: FIX Activity=(Base FIX Activity)+[(Measured FIX Antigen−Base FIX Antigen)×(Patient's FIX Coefficient)].

Therefore, for this patient we determined the FIX level after Alprolix to be:

(0%+[(64.33 IU/dL−6.1 IU/dL)×(1.1)]=59.33%

These results were clinically comparable to the measured FIX Activity (Table 4).

TABLE 4

Determination of FIX Level in a Patient with Severe Hemophilia B.

| Time Points | Baseline FIX Activity (Historical) | Baseline FIX Antigen (Calculated) | Measured FIX Antigen (FIX:Ag) (24 h after Alprolix) | FIX Activity (Calculated) | FIX Activity (Measured) |
|---|---|---|---|---|---|
| Imputed Baseline Presentation* | <1% | 6.1 IU/dL | | | |
| | | | 8.0 IU/dL | | 4% |
| 24 hrs after Alprolix | | | 64.33 IU/dL | 59.33% | 55% |

6 days after Benefix

Example 3: Determination of Von Willebrand Factor (VWF)

Deficiencies in the essential clotting protein, von Willebrand Factor (VWF), result in von Willebrand Disease (VWD). VWF Activity is most commonly assessed clinically using the VWF Ristocetin Cofactor Assay (VWF:RCo).

Measurement of VWF:

Blood samples were collected by venipuncture in 3.2% sodium citrate anticoagulant. Platelet poor plasma was separated by centrifugation per clinical protocols, snap frozen, and stored at −80 C until tested. VWF-deficient plasma (Affinity Biologicals), pooled normal plasma (Precision Bio-Logic), and plasma from anonymous healthy donors were used as controls.

VWF Antigen for Case #1 was detected by STA Liatest VWF:Ag (Stago) per the clinical laboratory protocols of the Bloodworks Northwest Hemostasis Reference Laboratory.

VWF Antigen was detected in Case #2 by dotblot. Samples were diluted in VWF-deficient plasma (Affinity Biologicals), blotted to nitrocellulose membrane (Bio-Rad), VWF detected using standard Western blot protocols using HRP-conjugated rabbit anti-human VWF antibody (DAKO), and densitometry performed using ImageQuantTL (GE Healthcare).

VWF activity was measured by VWF ristocetin cofactor activity (VWF:RCo) in the Bloodworks Northwest clinical hemostasis laboratory per CLIA-approved clinical protocols.

The Humate-P (CSL Behring) drug coefficient was determined by measuring VWF Antigen and VWF Activity in two patients with VWD who received Humate-P for clinically indicated kinetic studies which performed VWF Antigen and VWF Activity at serial time points. The patients' baseline VWF parameters were then subtracted from the post-Humate-P dosing data. The excess VWF levels were plotted (antigen vs. activity) to determine the Humate-P coefficient.

The Koate DVI (Kedrion Biopharma) drug coefficient was determined by serial dilution of Koate DVI into VWF-deficient plasma (Affinity Biologicals), both VWF Antigen and VWF Activity were performed, and the ratio of Activity:Antigen calculated.

Determination of VWF Levels in Patients Receiving VWF-Containing Drugs:

VWF Case #1

A 51 year old woman with VWD presented for a clinically indicated kinetic study of Humate-P, a VWF replacement therapy. The patient had blood samples drawn at baseline (prior to Humate-P), and at 1, 2, 4, and 6 hours after Humate-P infusion. VWF Antigen was measured by ELISA, and VWF Activity was measured by VWF ristocetin cofactor assay. Her baseline VWF Antigen was 31 IU/dL, and her baseline VWF Activity was 6%. VWF Antigen was 179 IU/dL at 4 hours, and 160 IU/dL at 6 hours. The VWF Antigen was too high (out of range of the assay) at the 1 and 2 hour time points. The Humate-P drug coefficient was determined to be 0.4.

We used this information to determine the VWF Activity by: VWF Activity=(Baseline VWF Activity)+[(Measured VWF Antigen−Baseline VWF Antigen)×(Humate-P Coefficient)].

Thus, for this patient, the VWF Activity levels were determined to be:

4 Hours after Humate-P:(6%)+[(179 IU/dL−31 IU/dL)×(0.4)]=65.2%

6 Hours after Humate-P:(6%)+[(160 IU/dL−31 IU/dL)×(0.4)]=57.6

These results were clinically comparable to the measured VWF Activity (Table 5).

TABLE 5

Determination of VWF Activity in a Patient with von Willebrand Disease.

| Time Point | Baseline VWF Activity (VWF:RCo) | Baseline VWF Antigen (VWF:Ag) | VWF Antigen (VWF:Ag) | VWF Activity (Calculated) | VWF Activity (Measured VWF:RCo) |
|---|---|---|---|---|---|
| Baseline | 6% | 31 IU/dL | | | |
| 1 Hr after Humate-P | | | >200 IU/dL | *OOR | 121% |
| 2 Hrs after Humate-P | | | >200 IU/dL | *OOR | 100% |
| 4 Hrs after Humate-P | | | 179 IU/dL | 65.2% | 62% |
| 6 Hrs after Humate-P | | | 160 IU/dL | 57.6% | 54% |

*OOR = Out of Range of the Assay (High)

VWF Case #2

A 28 year old male with severe hemophilia A presented for a clinically indicated kinetic study of Koate DVI. In addition to FVIII, Koate DVI, a plasma derived product, also contains VWF. The patient had a blood sample taken at baseline and at 1 hour, 4 hours, and 24 hours after Koate DVI infusion. We detected VWF Antigen by dot blot, a sensitive paper-based method adaptable to point-of-care (Results in FIG. 1).

We determined the patient's baseline VWF Antigen to be 79.98 IU/dL, and his Baseline VWF Activity (VWF ristocetin cofactor activity, or VWF:RCo) to be 53%. VWF Antigen was 101.83 IU/dL 24 hours after Koate DVI infusion, but values were above the range of the dot blot at the one and four hour time points. We experimentally determined the VWF Drug Coefficient of Koate DVI to be 0.98. We determined the patient's VWF Activity (VWF:RCo) at the 24 hour time point by:

VWF:RCo=(Base VWF:RCo)+[(Measured VWF:
Ag−Base VWF:Ag)×(Koate DVI Coefficient)].

Therefore, the VWF Activity at 24 hours was determined to be:

(53%)+[(101.83 IU/dL−79.98 IU/dL)×(0.98)]=74.4%

This result was clinically comparable to the measured VWF:RCo Activity (Table 6).

TABLE 6

Determination of VWF in a Patient Receiving Koate DVI.

| Time Point | Baseline VWF Activity (VWF:RCo) | Baseline VWF Antigen (VWF:Ag) | VWF Antigen (Measured) | VWF Activity (Calculated) | VWF Activity (Measured VWF:RCo) |
|---|---|---|---|---|---|
| Baseline | 53% | 79.98 IU/dL | | | |
| 1 Hr After Koate DVI | | | OOR* | | 398% |
| 4 Hrs After Koate DVI | | | OOR* | | 166% |
| 24 Hrs After Koate DVI | | | 101.83 IU/dL | 74.4% | 76% |

*OOR = Out of Range of the Assay (High)

Example 4: Determination of Factor VII (FVII) and Factor XI (FXI)

Patients with deficiencies of FVII or FXI (also known as Hemophilia C) are rare. We determine FVII and FXI levels in deficient plasma using experimentally derived factor coefficients and measured Factor Antigen levels.

Measurement of FVII and FXI:

Commercially-available normal and abnormal (FVII- and FXI-deficient) plasmas (Siemens) were obtained to be tested as experimental samples. Factor VII and Factor XI Coefficients were determined by serial dilution of normal reference plasma (Precision BioLogic) into FVII-deficient and FXI-deficient plasmas (Affinity Biologicals).

Factor VII Antigen was determined by ELISA (FVII-AG ELISA kit, Affinity Biologicals) per the manufacturer's instructions. FXI Antigen was determined by ELISA (FIX-EIA paired antibodies, Affinity Biologicals) per the manufacturer's instructions. FVII and FXI activities were determined via manual one-stage assay per the clinical protocols of the Bloodworks Northwest Hemostasis Reference Laboratory.

Determination of FVII in Plasma:

We tested two plasma samples, one with normal levels of FVII and one deficient in FVII (approximately 1/3 FVII activity). We experimentally determined that the coefficient of normal FVII is 1.12. The FVII Activity was then determined by: FVII Activity=[(Measured FVII Antigen)×(FVII Coefficient)].

We determined the FVII Activity in the plasma samples using the FVII Antigen result:

For Normal Plasma:(80.13 IU/dL)×(1.12)=89.74%

For FVII Deficient Plasma:(33.79 IU/dL)×
(1.12)=37.84%

These results were clinically comparable to the measured FVII activity (Table 7).

TABLE 7

Determination of FVII in Deficient Plasma.

| Sample | FXI Antigen (Measured) | FXI Activity (Calculated) | FXI Activity (Measured) |
|---|---|---|---|
| Normal Plasma | 80.13 IU/dL | 89.7% | 94.5% |
| FVII-Deficient Plasma | 33.79 IU/dL | 37.8% | 36.7% |

Determination of FXI in Plasma:

We tested two plasmas, one with normal levels of FXI, and one deficient in FXI (approximately 1/3 FXI activity). We experimentally determined using plasma pooled from healthy subjects that the coefficient of natural FXI is 0.82. The FXI Activity was then determined by: FXI Activity= [(Measured FXI Antigen)×(FXI Coefficient)].

We then determined the FXI Activity in the plasma samples using the FXI Antigen result:

For Normal Plasma:(111.5 IU/dL)×(0.82)=91.43%

For FXI Deficient Plasma:(43.7 IU/dL)×(0.82)
=35.83%

These results were clinically comparable to the measured FXI activity (Table 8).

TABLE 8

Determination of FXI in Deficient Plasma.

| Sample | FXI Antigen (Measured) | FXI Activity (Calculated) | FXI Activity (Measured) |
|---|---|---|---|
| Normal Plasma | 111.5 IU/dL | 91.4% | 103.1% |
| FXI-Deficient Plasma | 43.7 IU/dL | 35.8% | 29.4% |

Care for patients at-risk for bleeding involves therapies directed at replacing clotting factor deficiencies. However, the clotting factor activity assays which inform treatment decisions are time consuming, technically challenging, and are limited to highly specialized clinical laboratories. Coagulation factor level determination using this method should be superior to current care as this method can provide data in real time to inform medical decision making. For example, many patients who are at-risk for bleeding are treated in facilities where there is not a readily accessible STAT option in the reference coagulation laboratory, or no reference coagulation laboratory is available at all. This methodology could be used to assess a factor level in diverse settings, which would give the patients more choice in their locations of care and enable more precise treatment for safer procedures and bleeding episode management. Our methodology would also allow well-characterized bleeding disorder patients to use data to determine their actual level at home, rather than just estimating dosing from the time since their last drug dose. For example, a patient could see if his level was where it needed to be before he went to play soccer, but conserve factor use when his level is satisfactory for a low-risk, sedentary day at the office. A real time factor level assessment provides numerous advantages over current practice by accounting for multiple potential confounders (including individual variance drug kinetics, multiple drug exposures, and diverse underlying disease mechanisms) and allows for precise dosing decisions during periods of active bleeding, when clotting factors can be rapidly consumed. We anticipate that precise treatment of bleeding informed by real time factor level information will result in more effective control of bleeding and more rapid transitions to healing.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for identifying and treating a subject that has or is at risk of having a bleed, comprising:
    obtaining data representing a baseline coagulation factor protein level ($Base_{Ag}$) from a subject;
    measuring a coagulation factor protein level ($Measured_{Ag}$) in a sample at point of care from the subject using one or more coagulation factor-specific molecules, wherein the one or more coagulation factor-specific molecules are antibodies;
    obtaining data representing the subject's baseline coagulation factor activity level ($Base_{Act}$);
    generating a coagulation factor activity score by mathematically combining the $Measured_{Ag}$, $Base_{Ag}$, and $Base_{Act}$, wherein the coagulation factor activity score is indicative of the subject's real time coagulation factor activity;
    identifying that the subject has or is at risk of having a bleed based on the coagulation factor activity score; then administering a drug coagulation factor to the subject.
2. The method of claim 1, wherein the score is generated by a computer processor.
3. The method of claim 1, wherein the coagulation factor is Factor VIII (FVIII), Factor IX (FIX), fibrinogen, fibrin, prothrombin, thrombin, Factor II (FII), Factor V (FV), Factor VII (FVII), Factor X (FX), Factor XI (FXI), Factor XIII (FXIII), von Willebrand Factor (VWF), Factor XII (FXII), prekallikrein (PK), kallikrein, high molecular weight kininogen (HMWK), Tissue Factor (TF), Tissue Factor Pathway Inhibitor (TFPI), plasminogen, plasmin, plasminogen activator inhibitor -1 and -2 (PAI-1 and PAI-2), antithrombin III (ATM), protein C (PC), protein S (PS), tissue plasminogen activator (tPA), urokinase, alpha-2 antiplasmin, alpha-2 macroglobulin, thrombin activatable plasmin inhibitor (TAFI), thrombomodulin, or ADAMTS13 (a disintegrin and metalloproteinase with thrombospondin motifs-13).
4. The method of claim 1, wherein the sample is a blood sample, blood component, saliva, or urine.
5. The method of claim 4, wherein the blood component is plasma, serum, blood cells, blood cell fragments, or microparticles.
6. The method of claim 1, wherein the one or more coagulation factor-specific molecules are polyclonal antibodies.
7. The method of claim 1, wherein the one or more coagulation factor-specific molecules are monoclonal antibodies.
8. The method of claim 1, wherein the one or more coagulation factor-specific molecules are directly detected via a linked tag.
9. The method of claim 8, wherein the linked tag is a metal, chemical, or fluorescent tag.
10. The method of claim 1, wherein the $Measured_{Ag}$ is measured using one or more antibodies that detect the one or more coagulation factor-specific molecules.
11. The method of claim 1, wherein more than one coagulation factor is detected at the same time in a multiplex assay.
12. The method of claim 1, wherein more than one coagulation factor is detected at the same time using multiple parallel assays.
13. The method of claim 1, wherein the obtaining data representing $Base_{Ag}$ further comprises
    obtaining a sample derived from the subject, wherein the subject has not received a drug coagulation factor; and
    measuring $Base_{Ag}$ in the sample using the one or more coagulation factor-specific molecules.
14. The method of claim 1, wherein the obtaining data representing BaseAct further comprises obtaining $Base_{Act}$ from the subject's historical records.
15. The method of claim 1, wherein the mathematically combining comprises using the following formula:

$$\text{coagulation factor activity score} = Measured_{Ag} \times (Base_{Act}/Base_{Ag}).$$

16. The method of claim 1, further comprising:
    obtaining data representing a drug coefficient ratio ($Drug_{Act:Ag\ Ratio}$) of the drug coagulation factor, wherein the $Drug_{Act:Ag\ Ratio}$ Ratio is derived from the drug coagulation factor activity level ($Drug_{Act}$) and from the drug coagulation factor protein level ($Drug_{Ag}$), wherein the $Drug_{Act}$ and the $Drug_{Ag}$ have been measured experimentally.
17. The method of claim 16, further comprising
    measuring a second protein level of the coagulation factor ($Measured_{Ag}2$) after the treating, and
    generating a second coagulation factor activity score,
    wherein the second coagulation factor activity score is derived from the formula:

$$(Base_{Act}) + [(Measured_{Ag}2 - Base_{Ag}) \times (Drug_{Act:Ag\ Ratio})].$$

18. The method of claim 16, wherein the drug coagulation factor is a blood component clotting factor; blood component-derived clotting factor; recombinant clotting factor; recombinant activated clotting factor; or biochemically modified recombinant clotting factor.
19. The method of claim 17, wherein the second coagulation factor activity score is used to determine a further dose of the drug coagulation factor to be administered to the subject.
20. The method of claim 1, wherein the bleeding disorder is inherited or acquired.

21. The method of claim 1, wherein the bleeding disorder is hemophilia A, hemophilia B, or von Willebrand Disease (VWD).

22. The method of claim 1, wherein the subject is at risk of having a bleeding disorder due to: medication exposure; anti-coagulation drug therapy; medical exposure; exposure to extracorporeal circuits; exposure to artificial valves; exposure to vascular shunts; exposure to temporary or permanent implantable vascular devices; medical conditions;
 vitamin K deficiency; cancer; liver failure; renal failure; development of antibodies in response to clotting factor therapy; or development of autoantibodies targeting one or more clotting factors.

\* \* \* \* \*